United States Patent
Trotta

Patent Number: 5,433,713
Date of Patent: Jul. 18, 1995

[54] POLYETHERAMIDE TUBING FOR MEDICAL DEVICES

[75] Inventor: Thomas Trotta, Miami, Fla.

[73] Assignee: Cordis Corporation, Miami Lakes, Fla.

[21] Appl. No.: 96,218

[22] Filed: Jul. 22, 1993

Related U.S. Application Data

[63] Continuation of Ser. No. 685,440, Apr. 15, 1991, abandoned.

[51] Int. Cl.⁶ .................. A61M 5/00; A61M 25/00
[52] U.S. Cl. .................. 604/264; 604/93; 604/96; 604/280; 606/191; 606/194
[58] Field of Search .................. 604/95–96, 604/281–282, 264, 280, 93, 104–106; 606/191–194, 196–198

[56] References Cited

U.S. PATENT DOCUMENTS

| | | |
|---|---|---|
| 4,100,309 | 7/1978 | Micklus et al. |
| 4,119,094 | 10/1978 | Micklus et al. |
| 4,356,300 | 10/1982 | Isler et al. |
| 4,563,181 | 1/1986 | Wijayarathna et al. |
| 4,585,666 | 4/1986 | Lambert. |
| 4,636,346 | 1/1987 | Gold et al. |
| 4,743,258 | 5/1988 | Ikada et al. |
| 4,835,003 | 5/1989 | Becker et al. |
| 4,886,506 | 12/1989 | Lovgren et al. |
| 4,898,591 | 2/1990 | Jang et al. .............. 604/282 |
| 4,917,667 | 4/1990 | Jackson .............. 604/96 |
| 4,950,257 | 8/1991 | Hibbs et al. .............. 604/264 |

FOREIGN PATENT DOCUMENTS

1600963 5/1978 United Kingdom.

OTHER PUBLICATIONS

The Merck Index, 1976, p. 875, Ninth Edition.
*Handbook of Thermoplastic Elastomers*, Second Edition, Walker and Rader, Van Nostrand Reinhold Company, New York, "Polyamide Thermoplastic Elastomers", Farrissey and Shah, pp. 258, 259.
"The Use of Hydromer Coatings on Medical Devices", Lorenz, The Medical Plastics Technology Seminar, Oct. 4, 1984.

*Primary Examiner*—C. Fred Rosenbaum
*Assistant Examiner*—Ronald K. Stright, Jr.
*Attorney, Agent, or Firm*—Lockwood, Alex, Fitzgibbon & Cummings

[57] ABSTRACT

Medical device tubing is prepared from a blend of polyetheramide having substantially no ester linkages with either or both a polyamide and a polyesteretheramide. The resulting tubing has an exceptionally high burst strength to flexibility ratio, and migration of monomers to the surface resulting in blooming is substantially retarded.

13 Claims, 3 Drawing Sheets

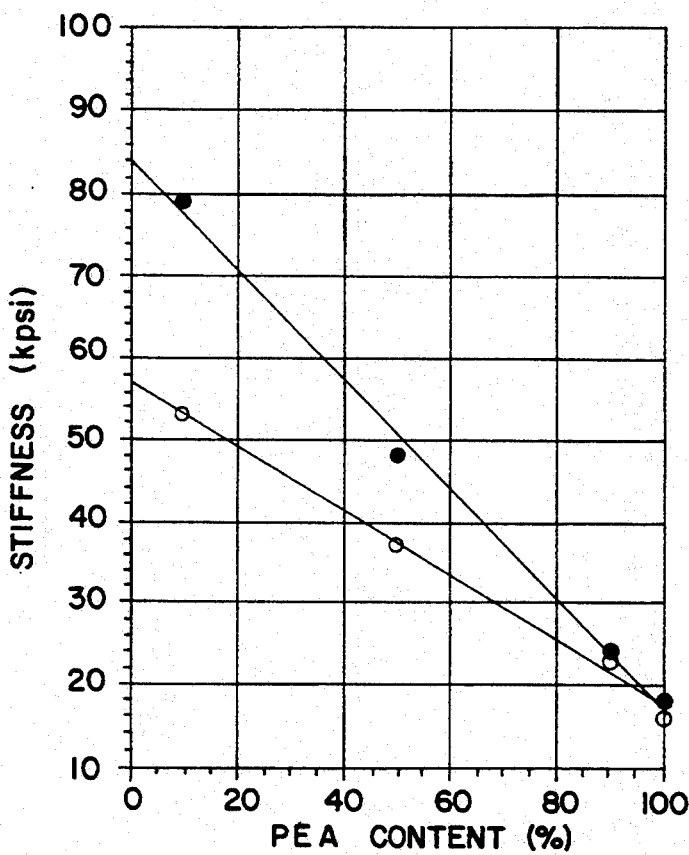
FIG. 4
○ AS EXTRUDED
● ANNEALED
FIG. 5
● ANNEALED
  70D BLENDS
○ AS EXTRUDED
  70D BLENDS
▼ ANNEALED
  PA BLENDS
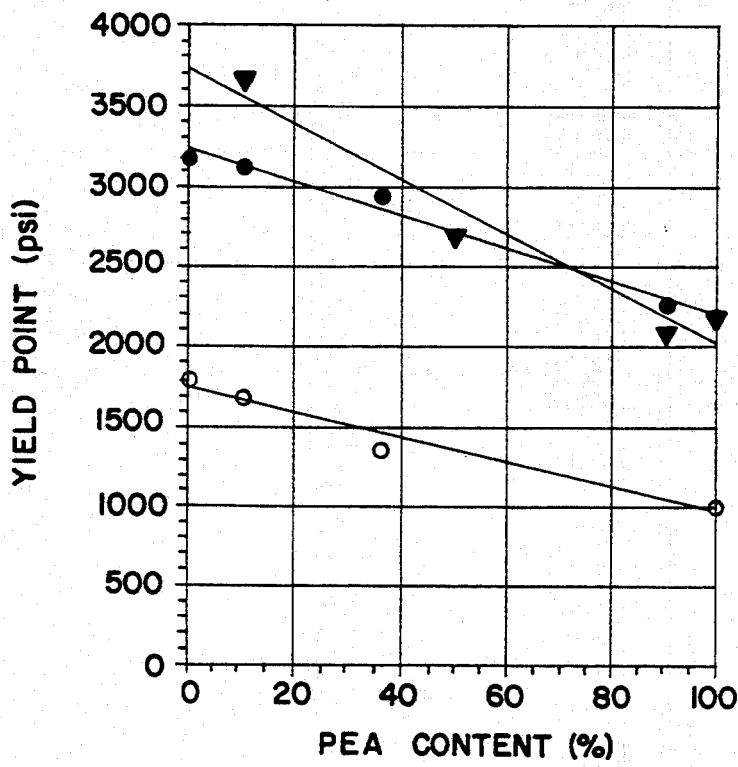

○ AS EXTRUDED
● ANNEALED

POLYETHERAMIDE TUBING FOR MEDICAL DEVICES

This application is a continuation of application Ser. No. 685,440, filed May 15, 1991 now abandoned.

BACKGROUND AND DESCRIPTION OF THE INVENTION

The present invention generally relates to medical devices, especially to tubing that exhibits improved properties which are especially suitable for various medical devices such as catheters and the like. More particularly, the invention relates to medical device tubing components which are extruded from a blend of at least two polymers, one of which is a polyetheramide. As used herein, the polyetheramide is one which has no ester linkages or has only incidental ester linkages, hereinafter referred to as having substantially no ester linkages. Advantageously, the polyetheramide component is blended with another polyamide-type of material in order to provide physical properties which are especially suitable for extrusion into catheter wall components and/or tip components. The polyetheramide-containing tubing is particularly suitable for medical device uses because the extruded polymer material exhibits excellent burst strength properties and good flexibility while at the same time retarding blooming that is experienced by other polyamide-types of tubing when they are stored for extended time periods.

Many medical devices incorporate tubing of various types and lengths. Often this tubing is intended for insertion into a living body, typically into and through body passageways such as those of the cardiovascular system, of the urethral tract, and the like. The most common type of this general grouping of medical devices are known as catheters, and they can incorporate tubing in body, balloon and tip members thereof. Exemplary catheters include those designed for angioplasty, valvuloplasty, urological uses, and the like. Typically, these devices are inserted into a body passageway such as the lumen of a blood vessel, a heart passageway, a urological passageway and the like, often with fluoroscopic guidance.

When medical devices are intended for use within the human body, certain parameters need to be satisfied. Usually the tubing must exhibit adequate flexibility so that, for example in the case of catheters, the tubing can easily wind its way through passageways which include bends and the like whereby the tubing can traverse a pathway through, for example, branching blood vessels. Furthermore, in many instances a catheter is manipulated from a proximal location outside of the body in order to position the distal portion of it in the vicinity of the administration or treatment location. In such systems or assemblies, it is important that the catheter exhibit adequate torque control so that it can be manipulated through narrow and branching passageways by radial movements and the like while having enough longitudinal or column resistance to negotiate through these passageways.

Another strength characteristic which is important for medical devices such as angiographic catheters, whether braided or unbraided, other balloon dilatation catheters and the like is burst strength. In some of these applications, fluids such as radiopaque dye containing fluids are injected under relatively high pressures through the medical device in a short time, for example, to provide a clear picture which is taken for a diagnostic purpose by an attending physician. This relatively high pressure injection achieves a high concentration of fluid in a short period of time so that images obtained during angiography and the like are as sharp as possible. Burst strength is also an important consideration for devices such as balloon catheters which include tubing components that are collapsed when inserted into the body cavity or the like and which are filled with a fluid so as to open up in a generally radial manner in order to open up a restricted passageway, for example, within the body. With these types of devices, an advantageous combination of high burst strength and flexibility are also important.

Quite a wide variety of materials have been used and proposed for manufacturing medical device tubing. Often, these materials are varied so that leading portions or tips of catheters and the like are somewhat more flexible and less traumatic than other portions of a catheter tubing which must be more responsive to manipulations that direct the device through the body. Exemplary in this regard is Ruiz U.S. Pat. No. 4,385,635, incorporated hereinto by reference. Certain approaches have been taken along these lines which concentrate on the use of polyamide types of materials for the manufacture of soft-tipped catheters, balloon catheters, catheter introducers, guiding catheters, vascular prostheses and the like. Included are Wijayarathna et al. U.S. Pat. No. 4,563,181, Lovgren et al. U.S. Pat. No. 4,886,506, Jang et al. U.S. Pat. No. 4,898,591, Jackson U.S. Pat. No. 4,917,667 and Hibbs et al. U.S. Pat. No. 4,950,257, each being incorporated by reference hereinto. These patents are representative of art relating to the use of polyether block amides, sometimes referred to by the designation PEBA. These are polyether-polyamide copolymers.

References such as the Wijayarathna et al. patent, the Jang patent and the Hibbs et al. patent explicitly teach that these polyether block amides are ester-linked polyether-polyamide copolymers which are described as being soft, rubbery polymeric materials. References such as these further indicate that these ester-linked polyether block amides are compatible with and fusible to polyamides or nylons by heat and pressure, while further indicating that the ester-linked polyether block amides can be blended with nylon polyamides such as Nylon 11, with different blends being suitable for different needs. For example, it is possible to blend these materials to provide a more flexible or softer extruded polymer that is more suitable for a tip portion of a catheter, while a different blend is less flexible and provides an extruded tubing that is more suitable for a catheter body requiring good torque control.

It has been found, however, that many of these polymers do not provide adequate burst strength properties and especially do not afford an extremely high burst strength to flexibility ratio which can be important for especially difficult medical device tubing applications. Another shortcoming of polymers or polymer blends such as the PEBA polyether block amide or ester-linked polyetherpolyamide copolymers is the development of undesirable blooming which develops in much of this tubing after it has been stored for lengths of time that can be experienced during the normal commercial channels through which medical devices pass. Accordingly, at times when a medical professional removes a catheter or the like from its sterilized packaging, a quite noticeable quantity of blooming can be evident on the surface of the catheter, which can significantly reduce the confidence level that the medical professional has in the catheter. This has the potential of being detrimental to the supplier of the catheter and may result in loss of current and/or future sales.

It is currently believed that this blooming phenomenon is a manifestation of migration of monomers to the surface of the polymeric tubing. A fine white powder forms on the surface of the tubing as it ages at room temperature or after it has been subjected to heat treatment. This surface powder formation has the potential of adding to the foreign matter which enters the bloodstream or the like when the medical tubing contacts or otherwise communicates with the bloodstream or other portion of the body. Whether or not this represents a possible medical detriment, it nevertheless creates a perception of a product that is less than perfect. This is, of course, something to be avoided by suppliers of medical devices. For at least that reason alone, blooming is a phenomenon that is undesirable, and its avoidance can substantially increase the usefulness and value of the medical device.

Blooming can be detrimental for another reason. It is often desirable to provide a catheter or the like with a coating that is designed to impart lubricity or enhanced biocompatibility to the catheter, or to provide a means for administering a drug or the like. Blooming can interfere with these types of coatings, interfering with their adherence to the entirety of the catheter.

The present invention provides medical device components, particularly tubing for catheters and the like. The components are made from a polyetheramide material which can be extruded into a desired medical device component. The polyetheramide is a polyamide elastomer having substantially no ester linkages. It is preferred that the polyetheramide be blended with at least one other material falling within the general category of polyamide structures. Included in the grouping of other materials are polymers having polyamide structures per se as well as certain polyesteretheramides, especially those having a particularly high hardness such as Shore 70D or harder. When extruded, for example into tubing, the result is a material that has an extremely high burst strength to flexibility ratio and that retards blooming.

It is accordingly a general object of the present invention to provide improved medical device components, particularly tubing for catheters and the like.

Another object of the present invention is to provide an improved material and method for extruding medical device tubing.

Another object of this invention is to provide improved medical device tubing which incorporates polyetheramide materials that do not have any substantial ester linkages present within the polyetheramide.

Another object of the present invention is to provide improved polyetheramide or polyetheramide composition that exhibits an extremely high burst strength to flexibility ratio when extruded into medical device tubing.

Another object of this invention is to provide an improved polyamide-like or polyamide composition that retards blooming or the migration of monomers to the surface of tubing or the like which is extruded from the material.

These and other objects, features and advantages of the invention will be clearly understood through a consideration of the following detailed description.

BRIEF DESCRIPTION OF THE DRAWINGS

FIG. 2 is a perspective view, partially broken away, of a catheter having a structure typical of a guiding catheter or the like;

FIGS. 4, 5, 6 and 7 are plots of data generated during testing specified in the Examples hereof.

DESCRIPTION OF THE PARTICULAR EMBODIMENTS

Medical devices according to this invention are most readily exemplified as catheter devices, each of which contains tubing that must be both flexible and strong and that will not experience excessive blooming. The drawings and disclosure hereof illustrate several catheter types of medical devices into which the present invention can be incorporated.

Figure 1:
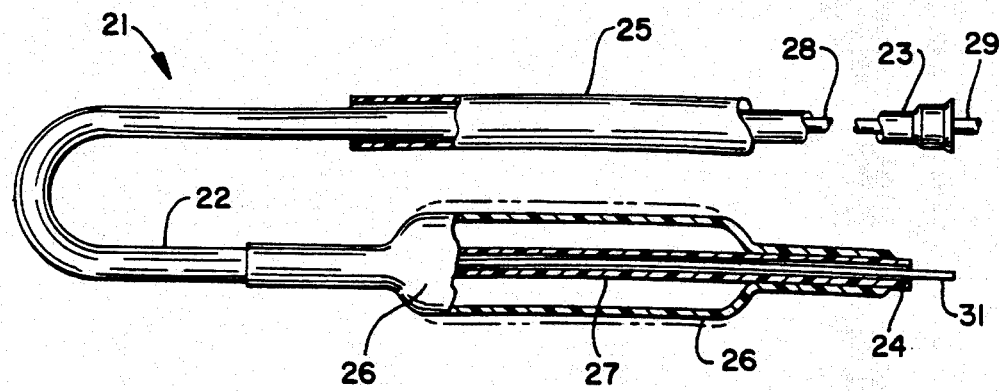
FIG. 1 is an elevational illustration, partially in cross section, of a catheter having a structure typical of one suitable for angioplasty.

An illustrative catheter is generally designated in FIG. 1 by reference numeral 21. Catheter 21 includes a catheter tube 22 having a proximal end 23 and a distal end 24. A guiding catheter 25 is also illustrated. A medical balloon 26 is shown secured to the distal portion of the catheter tube 22 in a location overlying one or more apertures 27 through the catheter tube. Extending through the lumen of the catheter tube 22 is an inner elongated body 28, such having a proximal end 29 and a distal tip end 31. The inner body 28 may be solid or have an internal lumen, depending upon the function that the inner body is to perform, whether it be simply a guiding function or whether it is intended to also provide the capability to insert materials into the bloodstream or measure parameters of the bloodstream, or the like.

These various components perform functions that are generally appreciated in the art. Typically with the aid of the guiding catheter 25, the inner body 28 and the catheter tube 22 are inserted into the cardiovascular system until the balloon is located at an occlusion site. At this stage, the balloon 26 is typically folded and collapsed, and it has an external diameter less than the inflated diameter illustrated in FIG. 1, to the extent that the balloon 26 is generally wrapped around the catheter tube 22. Once the balloon 26 is maneuvered to the location of the occlusion, a pressurized fluid is inserted at the proximal end 23 of the catheter tube 22 for passage through aperture 27 and for inflation of the balloon 26. This unfolds the balloon until it presents a relatively smooth outer surface or working profile for imparting forces that are radially outwardly directed at the desired site within the body in order to achieve the desired result of lesion dilation, occlusion reduction or similar treatment.

Figure 2:
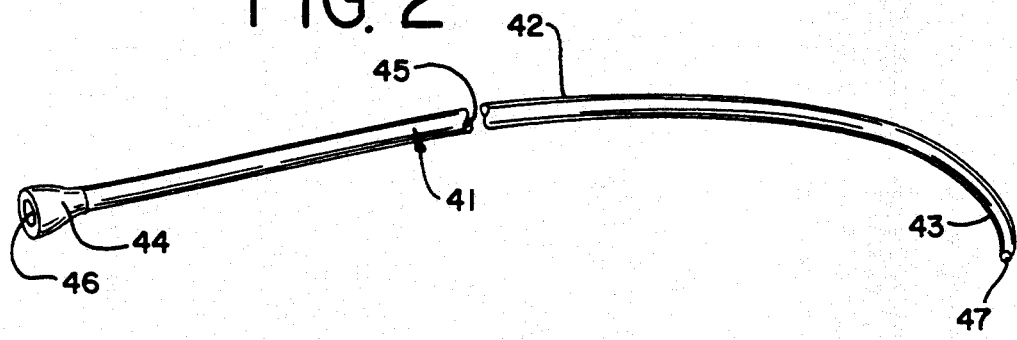

Another typical catheter, generally designated 41, which is on the order of guiding catheter 25 of FIG. 1, is illustrated in FIG. 2. Included is an elongated body portion 42, a tip portion 43, and a hub 44. A longitudinal lumen 45 extends throughout the elongated tubular body 42 and the tip portion 43, such longitudinal lumen 45 extending from a generally coaxial bore 46 in the hub 44 to a distal orifice 47 within the tip portion 43. Lumen 45 preferably has lubricous characteristics, and it is sized and structured to facilitate passage completely therethrough of an appropriate intravascular catheter or the like.

Figure 3:
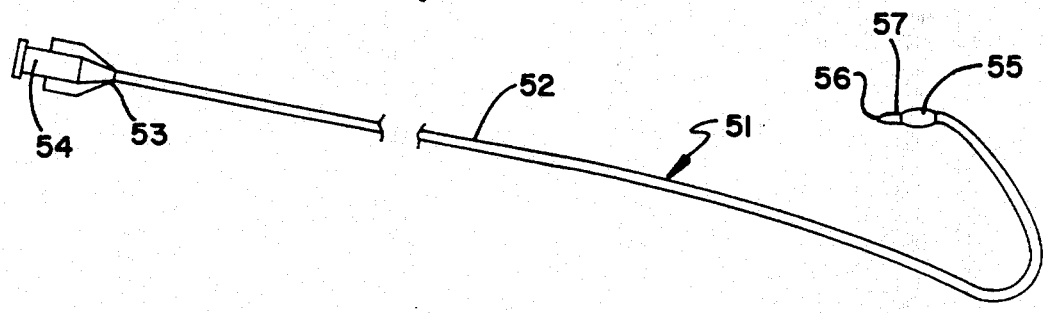
FIG. 3 is an elevational view, partially broken away, of a catheter having a structure typical of one suitable for use as an angiography catheter.

The catheter generally designated 51 in FIG. 3 is typical of one designed for use as an angiography catheter having a so-called Judkins curve tip. Other, non-illustrated catheter types, shapes, sizes and tip configurations can be practiced in accordance with this invention. The FIG. 3 catheter includes a catheter body or tube 52 that extends from a proximal end portion 53 at or within a proximal fitting 54 to a distal end portion 55 terminating at a distal or terminal end 56. A soft distal end member or tip 57 is included attached to the catheter tube 52 at the distal end portion 55 with the objective of inhibiting damage to arteries and vessels and the like when the catheter 51 is introduced into the vascular system in accordance with known surgical procedures.

Whatever form is taken by the devices according to this invention, they each include a tubing component which had been extruded from the polymer discussed herein which includes a polyetheramide (PEA or PETA) component, typically blended with a polyamide-type of component as discussed herein.

The polyetheramide component is generally categorized as a polyamide elastomer, and it has been found to possess properties that are especially exceptional for short dwell time medical devices. It has been found to offer a high strength to flexibility ratio and does not exhibit blooming of particles upon aging. For certain applications, it can be suitable for extruding into medical device tubing. In other instances, such as when modified flexibility or higher tensile strength values are desired, it has been found that these shortcomings of polyetheramides can be substantially removed by blending with other polyamide types of materials in order to greatly extend the flexibility range while retaining the unique, advantageous properties of the polyetheramide material. It has been found that, when certain of these polyamide-types of materials are blended with a polyetheramide, the result is a polymer blend which, when extruded, enjoys the properties of good flexibility while maintaining an extremely high burst strength to flexibility ratio and while maintaining bloom retardation properties which persist even upon substantial aging.

The polyetheramide (PEA or PETA) according to this invention is a polyamide elastomer in which there are virtually no ester linkages in that the bonds between the hard and soft segments are amides. These materials are also free from monomeric plasticisers, and they have a high hydrolysis stability. Exemplary materials in this regard are available from EMS-Chemie AG or Emser Industries. Exemplary trade designations are Grilamid ® ELY 60, which is especially preferred, and Grilon ® ELX 23 NZ, which are substantially ester-free polyetheramides comprising bis(3-aminopropyl)-polyoxytetramethylene glycol units, dimeric fatty acid units and caprolactam units, more particularly described by the formula below.

Polyetheramides typically are prepared by directly reacting an amine-terminated soft segment with a dimer acid and caprolactam. As an example in this regard, when the amine-terminated soft segment is bis(3-aminopropyl)polyoxytetramethylene glycol, and when the dimer acid is an acid such as EMPOL 1010, (a dimerized fatty acid having a low level of mono and polycarboxylic acids and a high content of dicarboxylic acid available from Unilever Emery, Netherlands) a PEA or PETA polymer of the following structure is formed:

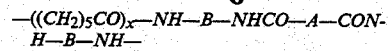

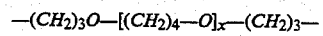

wherein A designates dimer acid segments, B designates $$-(CH_2)_3O-[(CH_2)_4-O]_x-(CH_2)_3-$$

and x is an integer greater than 1. It will be noted that these formulas contain no ester linkages.

When it is desired to blend this polyetheramide material with the other polyamide-types of materials discussed herein, this polyetheramide having substantially no ester linkages will be present at between about 10 and about 90 percent by weight, based upon the total weight of the polymer blend. Typically any such blend will include between about 10 and about 90 percent by weight, based upon the total weight of the polymer blend, of a flexibility modifying polyamide type of material.

With more particular reference to the flexibility modifying polyamide-types of material, they can typically fall into two different categories, one being a polyamide per se, and the other being a polyesteretheramide, both of which have been found to decrease the flexibility of the polyetheramide. In the case of the polyesteretheramides, it is especially preferred that same exhibit a shore hardness of 70D or harder. Polyamides include the nylons such as Nylon 6, Nylon 11, Nylon 12 and the like as well as materials such as Grilamid L25, a food contact approved grade of nylon 12 polyamide without additives or stabilizers. The general structure of these types of polyamides is, of course, quite well known, the structure having recurring polyamide groups (—CONH—) as an integral part of the polymer chain. The typical polyamide is a high molecular weight polymer in which these amide linkages occur along the molecular chain.

Polyesteretheramides, unlike the polyetheramides of the present invention, typically do have ester linkages. It is thought that this ester linkage contributes significantly to the blooming phenomenon which is generally exhibited by these types of polyesteretheramide materials. Included are the PEBA materials, namely the polyether block amide or ester-linked polyether-polyamide copolymer materials, which are believed to have a structure as follows:

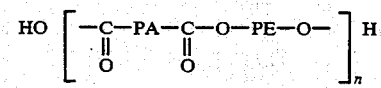

wherein PA is a polyamide, PE is a polyether, and n is an integer greater than 1 which represents the number of blocks of copolymer molecular units within the molecular formula of the copolymer. Representative polyesteretheramide materials include the PEBAX ® polyesteretheramide from ATOCHEM ® polymers. It has been found that, when the PEBAX ® polyetheresteramide from ATOCHEM ® polymers are utilized, the bloom retardation characteristic of this invention is accomplished when the shore hardness is equal to or harder than Shore 70D.

The polyetheramide having substantially no ester linkages can be blended with one or more of these additional polyamide-types of materials in order to thereby increase the stiffness of the polyetheramide. It has been found that this increased stiffness does not bring with it a detrimental reduction in the extremely high burst strength to flexibility ratio or the excellent blooming retardation which has been found to be experienced by polyetheramides that are extruded into medical device tubing components. However, at least the excellent bloom retardation property is not maintained when the polyetheramide having substantially no ester linkages is blended and extruded with a polyesteretheramide which has a shore hardness less than Shore 70D.

With further references to the aspect of the present invention wherein blooming or migration of monomers to the surface is retarded, this feature is particularly advantageous in those instances where a coating is applied, such as a hydrogel coating, to the extruded polymer tubing. It has been found that such blooming undermines coatings which are applied. Exemplary coating materials which have enhanced effectiveness in accordance with their combination with the other aspects of this invention include hydrogel materials. Exemplary hydrogel materials are copolymers of polyurethane and polyvinylpyrrolidone or cross-linked copolymers of polyethylene oxide and polyhydroxyethyl methacrylate. Exemplary hydrogel coatings are available from Hydromer Inc. under the registered trademark HYDROMER and are illustrated in Miklus et al. U.S. Pat. No. 4,100,309, incorporated by reference hereinto. Hydrophilic coatings having low friction properties are described, for example, in Lambert U.S. Pat. No. 4,585,666 and Becker et al. U.S. Pat. No. 4,835,003, incorporated by reference hereinto. The adherence of these types of coatings is detrimentally affected when blooming conditions are experienced. Generally speaking, the polyetheramide blended with the polyamide-type of material according to the invention has greater resistance to hydrolysis than the ester-linked polyetherpolyamide copolymer materials and than these copolymer materials blended with a polyamide per se.

The following examples illustrate some formulations and tests concerning the invention.

EXAMPLE 1

An outer tubing of a dilatation balloon catheter which utilizes a coaxial design was prepared. A blend of 36 weight percent of a polyetheramide (Grilamid ELY60) and 64 percent of a polyesteretheramide (Pebax 7033), having a hardness of Shore 70D, was blended in accordance with standard twin screw compounding technology. The extrusion was carried out in accordance with standard single screw extrusion technology in order to form an extruded tubing having an internal diameter of 0.039 inch and an external diameter of 0.046 inch. Thereafter, the extruded tubing was heat treated at 150° C. for 30 minutes. The result was a tubing having a high burst pressure to flexibility ratio. More specifically, the burst pressure of the tubing after 3 minutes at 37° C. was 420 psig, and the flexural modulus of the tubing according to ASTM 790 was 32 kpsi at 23° C.

COMPARATIVE EXAMPLE A

Tubing was extruded generally in accordance with Example 1, except the polyesteretheramide was Pebax 6333, having a hardness of Shore 63D. This particular polyesteretheramide polymer was found to have flexibility properties similar to the polymer blend of Example 1. Again, the extruded tubing was heat treated at 150° C. for 30 minutes. While the flexural modulus of the thus treated tubing was comparable with that of Example 1, 25 kpsi at 23° C. according to ASTM 790, the burst pressure of the tubing after 3 minutes at 37° C. was only 275 psi. In other words, this tubing had a much lower burst strength to flexibility ratio than did the Example 1 tubing.

COMPARATIVE EXAMPLE B

A polymer blend of polyamide and polyesteretheramide having a hardness of Shore 63D is used in medical devices. It has been observed that a fine white powder forms on the surfaces of this medical device tubing after aging at room temperature or after accelerated aging heat treatment procedures. This fine white powder undermines coatings, including hydrogels, applied to the medical device tubing.

EXAMPLE 2

A plurality of blends of a polyetheramide (Grilamid ELY 60) and of a polyamide (Grilamid L25) was used to prepare diagnostic catheter body material. Each blend was made in a one inch extruder using a groove feed throat and a low compression screw with a Maddox mixing section. Each polymer blend was extruded in a single strand and pelletized. The tubing was extruded on a laboratory scale three quarter inch extruder with a grooved feed throat and a standard polyethylene screw. The target dimension of the tubing was an internal diameter of 0.041 inch and an external diameter of 0.047 inch.

The tubing was tested on a CPQL Tinius Olsen stiffness tester in accordance with ASTM 747 at 37° C. These stiffness tests are reported in FIG. 4. Testing was conducted both as extruded and after annealing at 150° C. for 30 minutes. The extrusion of 100 percent polyetheramide had a stiffness of about 16 kpsi prior to annealing, with the stiffness ranging up to about 80 kpsi for annealed tubing extruded from a blend of about 10 percent polyetheramide and about 90 percent polyamide. This provides a range of stiffness which would be suitable for a variety of diagnostic catheter body requirements.

The formulations were also subjected to burst strength or yield point testing during which the tubing was subjected to a 37° C. water bath for two minutes, after which it was pressurized at 1 cc per minute until burst. The yield point data are reported in FIG. 5, with the triangular data points designating the annealed tubing in accordance with this Example. The data show exceptionally high burst pressure yield points and, when combined with the data of FIG. 4, illustrate an excellent burst pressure strength to flexibility ratio.

The tubing was subjected to accelerated aging testing by passing it through aging cycles as follows. Each aging cycle proceeded by subjecting the tubing to alternating humidity cycling, with one week at 60° C. and 90 percent relative humidity alternating with one week at 60° C. and 10 percent relative humidity. All ratios produced tubing with minimal or no particle generation, thereby exemplifying excellent retardation of bloom development.

EXAMPLE 3

Figure 6:
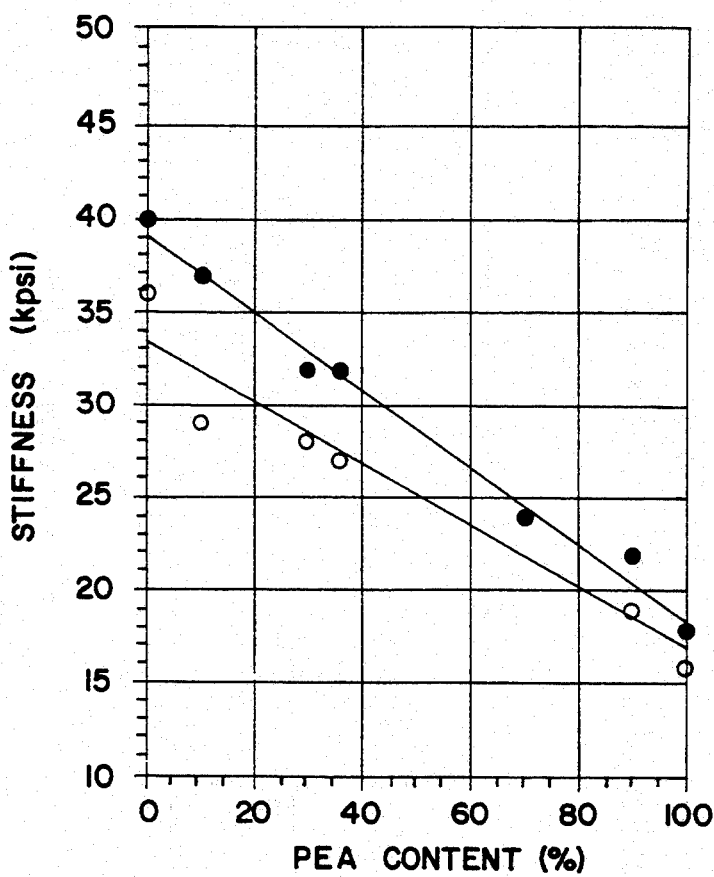

The procedure of Example 2 was followed, except this time the polyetheramide Grilamid ELY60 was blended with the polyesteretheramide Pebax 7033 having a hardness of Shore 70D. The result of the stiffness testing is reported in FIG. 6, and the yield point data are reported in FIG. 5 by the circular data points. In both cases, both the as extruded and as annealed data are reported. The data show exceptional high burst strength to flexibility ratios.

Figure 7:
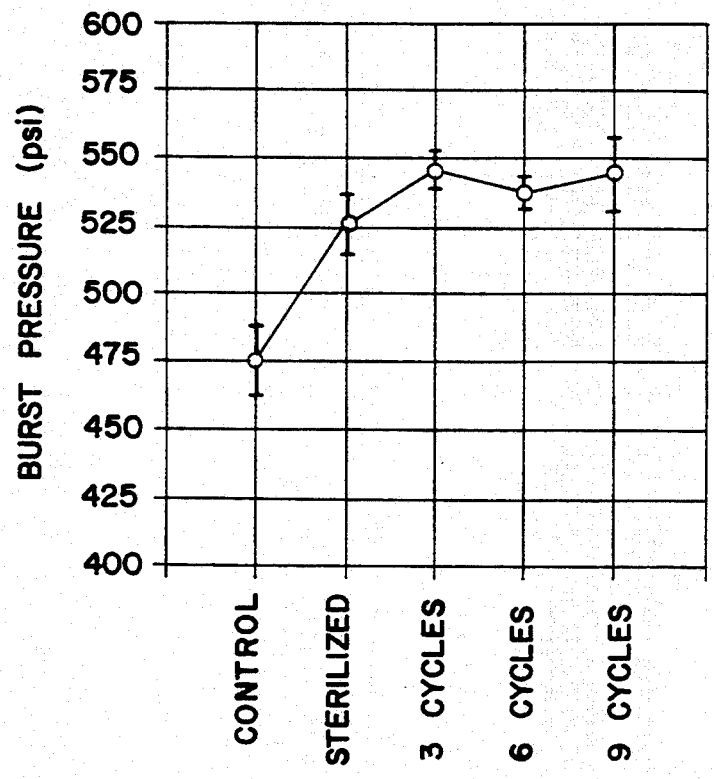

Accelerated aging tests were conducted as described in Example 2. FIG. 7 reports data for a blend of 36 percent polyetheramide having no ester linkages and 64 percent polyesteretheramide having a hardness of Shore 70D. An average of five samples were taken, and the vertical bar illustrated for each type of sample represents two standard deviations. The tubing was annealed at 150° C. for 30 minutes, then preconditioned and sterilized three times. In addition, the tensile properties were determined for these samples which had been subjected to accelerated aging conditions, and these data are reported in the Table.

TABLE

| Treatment | Ultimate Elongation (%) | Force at Break (psi) | Tensile Strength at Break (psi) |
|---|---|---|---|
| Control | 356 | 5.2 | 10,900 |
| 3 cycles | 366 | 5.4 | 10,900 |
| 6 cycles | 350 | 4.9 | 9,200 |
| 9 cycles | 376 | 5.2 | 9,700 |

In the FIG. 7 data, the "control" samples were untreated, and the "sterilized" samples were subjected to three conventional sterilization cycles. In the Table, the "control" was subjected to three sterilization cycles. In FIG. 7 and in the Table, "3 cycles" "6 cycles" and "9 cycles" refer to the aging cycles as described in Example 2. The data show that, even after accelerated aging, the excellent burst pressure and yield point at break are maintained even after this extensive aging which simulated typical storage aging of up to approximately 48 months. This was carried out by 9 aging cycles which is equivalent to storage for approximately 48 months at a 24° C. temperature. Furthermore, visual examination did not reveal any blooming until the 9th aging cycle was reached, at which point a small amount of powdering was detected on the interior of the tubing.

The polyetheramide and polyesteretheramide blended tubing described in this Example and that is of the type in respect of which the data of FIG. 7 and the Table are reported had a yield point to stiffness ratio of 0.10 at a stiffness value of 25 kpsi. Similar testing on Pebax 6333 (a polyesteretheramide having a hardness of Shore 63D) had a stiffness ratio of 0.08 at a stiffness of 25 kpsi.

It will be understood that the embodiments of the present invention which have been described are merely illustrative of a few of the applications of the principles of the present invention. Numerous modifications may be made by those skilled in the art without departing from the true spirit and scope of the invention.

I claim:

1. A medical device including a tubing component, said tubing component being an extruded polymer blend comprising:
   (a) between about 10 and about 90% by weight, based on the total weight of the polymer blend, of a polyetheramide having substantially no ester linkages, said polyetheramide having a structure defined by the formula:

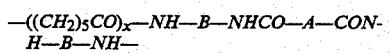
—((CH₂)₅CO)ₓ—NH—B—NHCO—A—CONH—B—NH— wherein A designates dimer acid segments, B designates —(CH₂)₃O—((CH₂)₄—O)ₓ—(CH₂)₃—, and x is an integer greater than 1; and
   (b) between about 10 and about 90% by weight based upon the total weight of the polymer blend, of a polyamide-type component that is a polyamide other than said polyetheramide and that excludes polyesteramides;
   whereby a substantially non-blooming tubing component exhibiting high burst strength to flexibility ratios is provided.

2. The medical device according to claim 1, wherein said medical device is an angiographic catheter incorporating said tubing component.

3. The medical device according to claim 1, wherein said catheter has a body and a tip, and said tubing component is a component of the body.

4. The medical device according to claim 2, wherein said catheter has a body and a tip, and said tip comprises said tubing component.

5. The medical device according to claim 1, wherein said polyamide includes a Nylon 12 polyamide.

6. The medical device according to claim 1, further including a coating applied to a surface of the tubing component.

7. The medical device according to claim 1, wherein said medical device is a balloon dilation catheter including a tubing portion with a distal end portion having a medical balloon secured to said distal end portion, and said tubing portion comprises said tubing component.

8. A medical device including a tubing component, said tubing component being an extruded polymer blend comprising:
   (a) between about 10 and 90% by weight based on the total weight of the polymer blend of a polyetheramide component having substantially no ester linkages, said polyetheramide component having a structure defined by the formula:

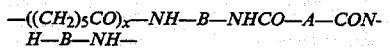
—((CH₂)₅CO)ₓ—NH—B—NHCO—A—CONH—B—NH— wherein A designates dimer acid segments, B designates —(CH₂)₃O—((CH₂)₄—O)ₓ—(CH₂)₃—, and x is an integer greater than 1; and
   (b) between about 10 and about 90% by weight based upon the total weight of the polymer blend, of a Nylon 12 polyamide-type component;
   whereby a substantially non-blooming tubing component exhibiting high burst strength to flexibility ratios is provided.

9. A medical device as defined in claim 8, wherein said medical device is an angiographic catheter incorporating said tubing component.

10. The medical device according to claim 9, wherein said catheter has a body and a tip, and said tubing component is a component of the body.

11. The medical device according to claim 9, wherein said catheter has a body and a tip, and said tip comprises said tubing component.

12. The medical device according to claim 8, further including a coating applied to a surface of the tubing component.

13. The medical device as defined in claim 8, wherein said medical device is a balloon dilatation catheter including a tubing portion with a distal end having a medical balloon secured to said distal end and said tubing portion comprises said tubing component.

* * * * *

UNITED STATES PATENT AND TRADEMARK OFFICE
CERTIFICATE OF CORRECTION

PATENT NO. : 5,433,713
DATED : July 18, 1995
INVENTOR(S) : Thomas Trotta

It is certified that error appears in the above-indentified patent and that said Letters Patent is hereby corrected as shown below:

Col. 1, line 6, delete "May" and insert --April--.
Col. 5, lines 61-62, insert a hyphen between "bis(3-aminopropyl)" and "polyoxytetramethylene"; line 63, delete the comma "," after "1010"; line 66, insert a comma after "Netherlands)".
Col. 6, lines 59-60, "polyetheresteramide from" should read --polyesteretheramide, from--.
Col. 9, line 29, insert a comma after " "3 cycles" "; line 45, 0.10 should not be in bold print; line 47, 0.08 should not be in bold print.

Signed and Sealed this

Twenty-ninth Day of October 1996

Attest:

BRUCE LEHMAN

*Attesting Officer*    *Commissioner of Patents and Trademarks*